United States Patent [19]

Bridges

[11] Patent Number: 5,171,562

[45] Date of Patent: * Dec. 15, 1992

[54] TURBINE AGGLOMERATED CALCIUM HYPOCHLORITE PARTICLE AND PROCESS FOR THE PRODUCTION THEREOF

[75] Inventor: William G. Bridges, Athens, Tenn.

[73] Assignee: Olin Corporation, Cheshire, Conn.

[*] Notice: The portion of the term of this patent subsequent to Mar. 24, 2009 has been disclaimed.

[21] Appl. No.: 542,279

[22] Filed: Jun. 22, 1990

Related U.S. Application Data

[63] Continuation of Ser. No. 898,841, Aug. 19, 1986, abandoned, which is a continuation-in-part of Ser. No. 749,164, Jun. 27, 1985, abandoned, which is a continuation-in-part of Ser. No. 717,983, Mar. 29, 1985, abandoned, which is a continuation-in-part of Ser. No. 639,052, Aug. 9, 1984, abandoned.

[51] Int. Cl.$^5$ ............... A01N 59/06; C01B 11/06
[52] U.S. Cl. ............... 423/474; 23/313 R; 252/186.37; 252/187.29
[58] Field of Search ........... 423/474; 252/186.2, 252/186.37, 187.28, 187.29; 23/313 R

[56] References Cited

U.S. PATENT DOCUMENTS

| | | | |
|---|---|---|---|
| 1,937,230 | 11/1933 | Kitchen | 423/474 |
| 2,195,754 | 4/1940 | Robson et al. | 23/293 R |
| 2,195,755 | 4/1940 | Robson et al. | 423/474 |
| 2,195,756 | 4/1940 | Taylor | 23/313 R |
| 2,901,435 | 8/1959 | Robson | 252/187.29 |
| 3,339,618 | 9/1967 | Bowden et al. | 159/48.1 |
| 3,544,267 | 12/1970 | Dychlada | 252/186.37 |
| 3,969,546 | 7/1976 | Saeman | 427/213 |
| 4,146,676 | 3/1979 | Saeman et al. | 428/403 |
| 4,276,349 | 6/1981 | Saeman | 428/403 |
| 4,328,200 | 4/1982 | Welch et al. | 423/474 |

OTHER PUBLICATIONS

Brochure on Turbulizer Turbine Agglomerator by Bepex Corporation.
Instruction, Operating and Service Manual on Turbulizer Turbine Agglomerator by Bepex Corporation.
Chemical Engineer's Handbook (5th Edition)–prepared by Robert H. Perry and Cecil H. Chilton–pp. 8-35, 8-36, 21-32 and 21-33–published by McGraw-Hill Book Company.
Kirk–Othmer Encyclopedia of Chemical Technology, 3rd Edition, vol. 21–Silver and Silver Alloys to Sulfolanes and Sulfones pp. 82-89 published by John Wiley and Sons.
Bepex Corporation, bulletin No. TR-35-Turbulizer--models and specifications.
Kirk–Othmer Encyclopedia of Chemical Technology, 3rd ed. John Wiley & Sons, 1983, vol. 21, pp. 77-81.

*Primary Examiner*—Jeffrey E. Russel
*Attorney, Agent, or Firm*—Ralph D'Alessandro

[57] ABSTRACT

A hydrated calcium hypochlorite agglomerated particle is provided that is produced in a turbine agglomerator and has a plurality of connecting links of recrystallized material bridging the small particles forming the agglomerate which has therein a plurality of pores created by the substantial evaporation of the layer of surface liquid. The surface tension and adhesion forces of the layer of surface liquid at least partially holds the agglomerated particle together prior to drying.

22 Claims, 9 Drawing Sheets

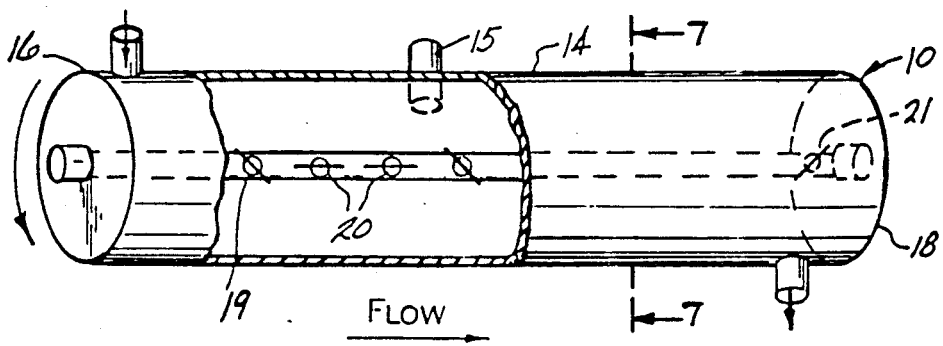
FIG-6
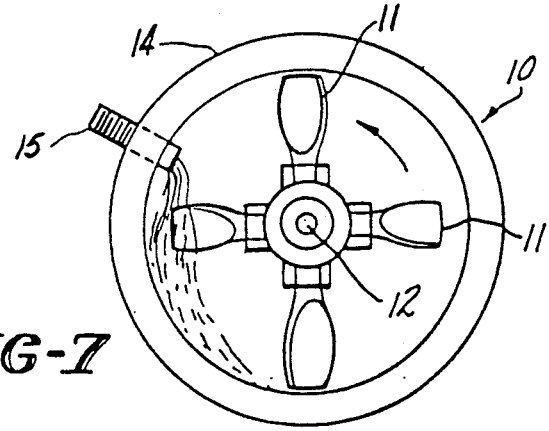
FIG-7
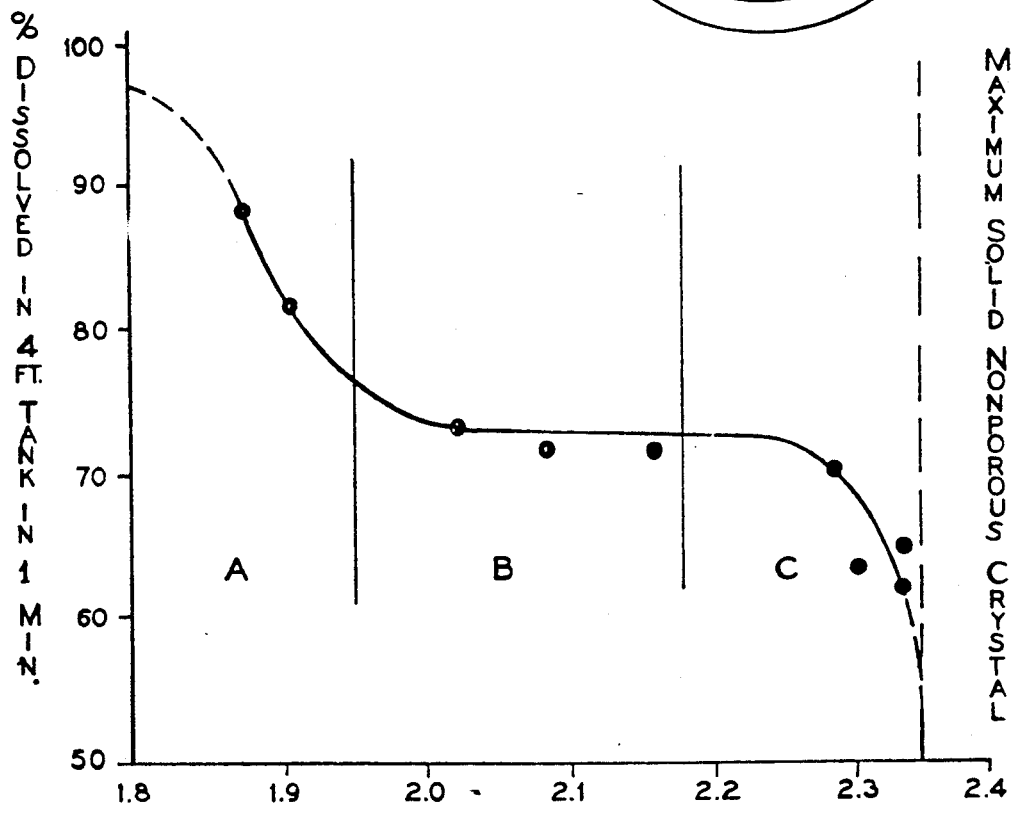
FIG-5 SPECIFIC GRAVITY, DISPLACEMENT g/ml

TURBINE AGGLOMERATED PRODUCT

TRAY DRIED PRODUCT

PLATELETS

COMPACTED PRODUCT

SPRAY GRAINED PRODUCT

TURBINE AGGLOMERATED CALCIUM HYPOCHLORITE PARTICLE AND PROCESS FOR THE PRODUCTION THEREOF

This application is a continuation of application Ser. No. 06/898,841 filed Aug. 19, 1986, now abandoned, which is a continuation-in-part of application Ser. No. 06/749,164 filed Jun. 27, 1985, now abandoned, which is a continuation-in-part of application Ser. No. 06/717,983 filed Mar. 29, 1985, now abandoned, which is a continuation-in-part of application Ser. No. 06/639,052 filed Aug. 9, 1984, now abandoned.

BACKGROUND OF THE INVENTION

This invention relates generally to a process for the manufacture of hydrated calcium hypochlorite. More specifically it is directed to the product particle produced by the use of a turbine agglomerator in a process to produce a highly porous calcium hypochlorite product with a fast dissolving rate.

Calcium hypochlorite compositions have been commercially utilized for a number of years as bleaching and sanitizing agents in water bodies, particularly in the sanitation and disinfection of swimming pool waters. Calcium hypochlorite's commercial appeal lies in the fact that it is a relatively stable and inexpensive solid oxidizing agent that uses its available chlorine to remove impurities and kill pathogenic organisms in water.

Calcium hypochlorite has been manufactured or proposed for manufacture from lime and sodium hydroxide by a number of processes. The different processes are either directed to reducing waste materials from the process or to produce the best quality product that is contaminate free in the most cost effective manner.

In most of the proposed hypochlorite, a commercially manufacturing calcium hypochlorite, a slurry is obtained containing crystals of calcium hypochlorite dihydrate in a concentrated aqueous solution of calcium hypochlorite and sodium chloride, or other inorganic halide. The slurry is then filtered to produce a cake containing from about 42 to about 48% by weight of water. When this cake is dried, a very light, porous cake is obtained which breaks down to an undesirable fine, dusty powder. The crystals in the cake lack natural cohesiveness. The filter cake can then be compressed, but the compressed cake, although harder, fragments into flaky granules with fragile edges. These granules are easily abraded and form an unsatisfactory dusty product. Alternately, the wet cake is partially dried, then compressed into a sheet between heavy rolls and further dried.

An alternate approach is the process of preparing calcium hypochlorite particles by admixing the wet cake of calcium hypochlorite in a cutting type mixer with dry fines in sufficient proportion to decrease the water content from the approximate 42 to about 48% by weight level down to a level of about 20 to about 30% by weight. Water is not evaporated during the mixing step, but rather the moist particles are dried in a separate step under carefully controlled conditions to avoid substantial crushing of the material. Compression pressures on the granules are less in this type of a mixer than with the aforementioned roll type of production. Therefore the mixer produced granules are softer. However, the granular particles so produced are not strong enough to resist dusting when subjected to severe handling conditions. In other techniques similar to this mixing technique, excessive dusting also has been a problem.

In all of the above-described calcium hypochlorite granulation techniques, drying is in devices such as a belt dryer or a tray type of dryer. A belt or tray type of dryer is used to minimize dust formation and dust entrainment in the drying atmosphere. Thermal degradation is a problem in these types of dryers, however, because the drying rates are relatively slow and calcium hypochlorite is thermally sensitive.

An alternate approach has been developed through the use of a spray graining technique to produce product granules. Generally, the spray-graining technique employs the spraying and drying of calcium hypochlorite slurries to avoid filtration and drying problems. This technique also minimizes the loss of calcium hypochlorite due to thermal degradation by reducing the required drying time. A key consideration in this technique is the fact that calcium hypochlorite is susceptible to rapid chemical decomposition in the presence of moisture at temperatures only slightly above ambient room temperatures. The thermal stability of calcium hypochlorite improves as the water content is reduced. Spray graining techniques have been perfected to produce granular calcium hypochlorite particles with layers of calcium hypochlorite encapsulated in a smooth rounded granule. However, the apparatus necessary to produce these granules in a fluidized bed or rolling bed dryer, as well as the necessary careful control of conditions, have made this a costly technique. Also, the use of a rotary drum results in the buildup of moist materials on the inner drum walls that requires labor intensive scraping of the walls to remove.

Further, the techniques adopted to produce calcium hypochlorite have not necessarily led to the production of a durable granule of a particular size and shape that dissolves quickly in water. Dust produced from the recycling of particles during the manufacturing process normally must be compacted. These compacted particles are normally dense. These and other particles cannot dissolve completely when the granules are distributed on the surface of a swimming pool. Undissolved residue in pools is undesirable in calcium hypochlorite product, being aesthetically displeasing and possibly leading to the bleaching out of the color in pool liners when the residue settles on the bottoms of the pools.

Further, the highly corrosive nature of calcium hypochlorite takes its toll on the apparatus employed in its production. Where pressure or preform rollers and granulators are employed, costly regular replacement or repair of the equipment must be accomplished every year or two since rapid oxidation of the exposed metallic parts occurs. The preform rollers press the partially dried and filtered cake into thick sheets at high pressures, for example up to 1000 pounds per square inch. The pressed sheets are then fed into the granulators where the sheets are broken up into small particles by rotary blades forcing the product through screens of predetermined size to create more surface area for drying. These screens and blades are especially susceptible to corrosion.

Other costly handling equipment, such as elevators and conveyors, must be used to transport the filtered cake and crushed particles to, between, and away from the compressive and granulating apparatus.

These and other problems are solved in the application of the process to produce the agglomerated product particle comprising the present invention.

SUMMARY OF THE INVENTION

It is an object of the present invention to provide a fast dissolving calcium hypochlorite product and a process to manufacture the product which generates less dust and uses fewer operating steps.

It is another object of the present invention to provide a highly porous calcium hypochlorite product and a process of manufacture the product that utilizes less heat energy in the evaporative or drying steps.

It is a feature of the product of the present invention that the product is produced by a process that employs a turbine agglomerator upstream of the final dryer and downstream of a separation device through which the slurry or paste used to manufacture the calcium hypochlorite passes.

It is another feature of the product of the present invention that feed material is centrifugally rotated and axially transported through the drum of a turbine agglomerator, being broken up and crushed by a shearing action and agglomerated into final product particles of desired size and moisture by the control of the layer of surface liquid such that the surface liquid comprises at least about 16 to about 26% of the particle weight before drying.

It is yet another feature of the product of the present invention that feed material is centrifugally rotated and axially transported through the drum of a turbine agglomerator, being crushed and broken into particles by a shearing action and agglomerated into final product particles of desired sizes, the final agglomerated product particles being formed from smaller particles or crystals that are interconnected by bridges or connecting links of calcium hypochlorite after drying.

It is another feature of the product of the present invention that fast dissolving, highly porous agglomerated product particles having a specific gravity of less than about 2.0 grams per milliliter as measured by displacement bulk density, and preferably less than about 1.95 grams per milliliter, are produced.

It is still another feature of the product of the present invention that the bulk density of the agglomerated product particles as measured by mercury porosimetry is less than about 1.39 g/ml.

It is still a further feature of the process of the present invention that water is added to the turbine agglomerator downstream of the axially oriented paddles to minimize compression of the product.

It is an advantage of the present invention that a fast dissolving product with high porosity is obtained so that substantially no undissolved residue remains in pool water and no bleaching out of pool liners on the bottoms of pools occurs.

It is another advantage of the present invention that the apparatus employed to make the product by the instant process requires less maintenance than the equipment traditionally employed in commercial processes.

It is still another advantage of the present invention that the product is produced with lower power costs and a resulting lower evaporative load from the use of more energy efficient equipment in a more efficient process.

It is yet another advantage of the present invention that more on-size final product particles are obtained from a dryer than in the traditionally employed prior commercial processes.

These and other objects, features and advantages are obtained in a porous agglomerated product particle of hydrated calcium hypochlorite with a fast dissolving rate produced by employing a turbine agglomerator upstream of the final dryer.

BRIEF DESCRIPTION OF THE DRAWINGS

The advantages of this invention will become apparent upon consideration of the following detailed disclosure of the invention, especially when it is taken in conjunction with the accompanying drawings wherein:

FIG. 5 is a graphic illustration of the dissolving rate of hydrated calcium hypochlorite particles screened to a 25-30 mesh size compared to particle density;

FIG. 6 is a diagrammatic illustration of the location of the moisture addition with respect to the paddles in a turbine agglomerator;

FIG. 7 is a sectional view taken along the lines 7—7 of FIG. 6 showing diagrammatically the positioning of the paddles and the moisture addition in a turbine agglomerator;

DETAILED DESCRIPTION OF THE PREFERRED EMBODIMENT

Figure 1:
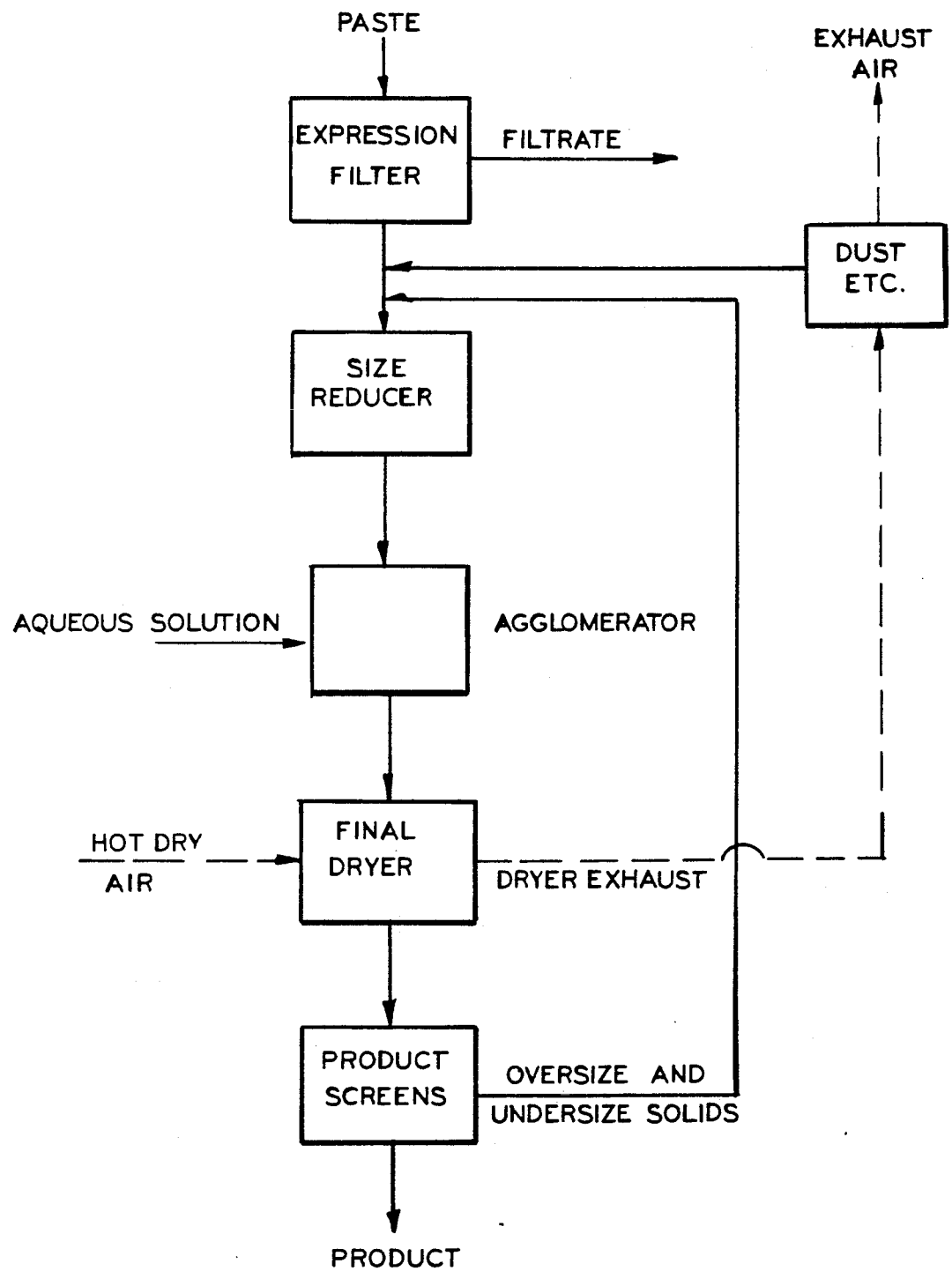
FIG. 1 is a diagrammatic illustration of the hypochlorite.

Hydrated calcium hypochlorite comprises calcium hypochlorite, $Ca(OCl)_2$, compositions having a water content in the range of from about 0.1 to about 15% by weight, and an available chlorine concentration of at least about 55%. The novel process of the present invention produces agglomerated hydrated calcium hypochlorite granules that are generally regular in shape, that is being generally rounded or spherical or aggregates of smaller, generally rounded particles.

The agglomerated hydrated calcium hypochlorite granules are produced by agglomeration in which agitation is employed. The agitation employed in this specific process is obtained by the use of a turbine agglomerator. This is apparatus that has a plurality of paddles mounted about a rotating shaft that extends axially through the turbine to mechanically blend moist feed particles and dry feed particles or feed particles and an agglomerating fluid. The paddles are arrayed in sets of generally four about the shaft, as seen in FIG. 7. The paddles 11 engage the feed material as they turn with the shaft 12 to centrifugally rotate the feed material and axially transport it through the drum 14 while achieving a shearing action which breaks up large clumps of the feed material. These paddles 11 also can compact the feed material.

A representative analysis of a typical calcium hypochlorite filter cake and a typical preferred analysis range for the calcium hypochlorite filter cake used as feed material in the instant process is shown in Table I. Alternate calcium hypochlorite feed material used commercially with, for example, an expression filter, can have a water component ranging from about 26 to about 40% by weight, while the calcium hypochlorite component of the feed material correspondingly can vary from about 67% to about 48% by weight and the NaCl from about 6% to about 12% by weight. The remaining components will vary slightly from those shown in Table I. The feed material used in the process to produce hydrated calcium hypochlorite can generally be stated to consist of calcium hypochlorite, water, sodium chloride and calcium salts selected from the group consisting of calcium chloride, calcium chlorate, calcium carbonate, and calcium hydroxide.

TABLE I

| Component | Typical Filter Cake Analysis Percent by Weight | Typical Analysis Range Percent by Weight |
| --- | --- | --- |
| Calcium hypochlorite | 45.43 | 42–48 |
| Calcium chloride | 0.44 | 0.0–1.5 |
| Calcium chlorate | 0.02 | 0.0–1.5 |
| Calcium hydroxide | 0.24 | 0.02–2.0 |
| Calcium carbonate | 0.44 | 0.1–2.0 |
| Sodium chloride | 7.75 | 6.0–8.0 |
| Water (difference) | 45.68 | 40–50 |

An agglomerated hydrated calcium hypochlorite granule of the instant process is produced by the agglomeration of small crystals or particles into an aggregate or larger particle of much greater porosity and much larger pores, or interstitial spacing, and surface deformation than is achieved with previous commercial processes. These fine particles, which typically are less than 40 mesh (less than 425 microns), are agglomerated in the turbine agglomerator or mixer 10 of FIG. 6. The turbine agglomerator 10 rotates at a fast enough rate to crush oversized feed particles to the proper or desired feed size of less than 40 mesh before the agglomeration zone, which is defined generally as the area in the drum 14 that is downstream of the point of water or liquid addition. The intense agitation caused by the rotation of the paddles in the agglomerator 10 also prevents overly large agglomerates from being formed. The final agglomerated product gives the appearance of an aggregate of smaller rounded particles. This lack of excessively oversized particles is significant for the ease and efficiency of the operation by minimizing the number of separate operational steps required in the process and, therefore, reducing the physical space, size and resulting cost of the apparatus necessary to employ the subject process.

Agglomeration by the instant process is achieved by providing the proper amount of binder to, in essence, glue the small, individual particles together in a manner that will be described in further detail hereafter. One method successfully employed to provide the proper amount of binder is to feed an overly wet mass of particles, such as particles of greater than 31% water by weight, to the turbine agglomerator while simultaneously blending dust or fines particles of less than 28% water by weight to achieve a final agglomerated particle with a discharge moisture of between about 19% to about 32%, preferably of between about 25% to about 31% and optimally of between about 28% and about 31% water by weight.

Another agglomeration method is to feed dry material with less than about 28% water by weight and blend in moisture in the form of water or other suitable solution or slurry into the turbine agglomerator to achieve the final desired agglomerated product having a moisture content of between about 19% to about 32%, preferably of between about 25% to about 31% and optimally of between about 28 to about 31% by weight. Still another method is to mill a material with about 28 to about 31% moisture by weight in the turbine agglomerator until an agglomerated particle of proper size and porosity is obtained.

The discharge products of turbine agglomerator 10 are dried to the desired moisture in an appropriate dryer, such as a tray dryer, a belt dryer, a fluid bed dryer or an energy efficient type of dryer. The dried agglomerated particles are then classified to the proper product size. Undersized and/or oversized material can be recycled into the turbine agglomerator for re-agglomeration to minimize additional compacting and crushing steps. Suitable particle sizes include those in the range from about 800 microns (20 mesh) to about 150 microns (100 mesh) and, preferably, from about 800 microns (20 mesh) to about 300 microns (50 mesh). The final product particles have a displaced bulk density which is at least about 1.0 grams per milliliter and, preferably, in the range from about 1.0 to about 2.0 grams per milliliter.

Figure 4:
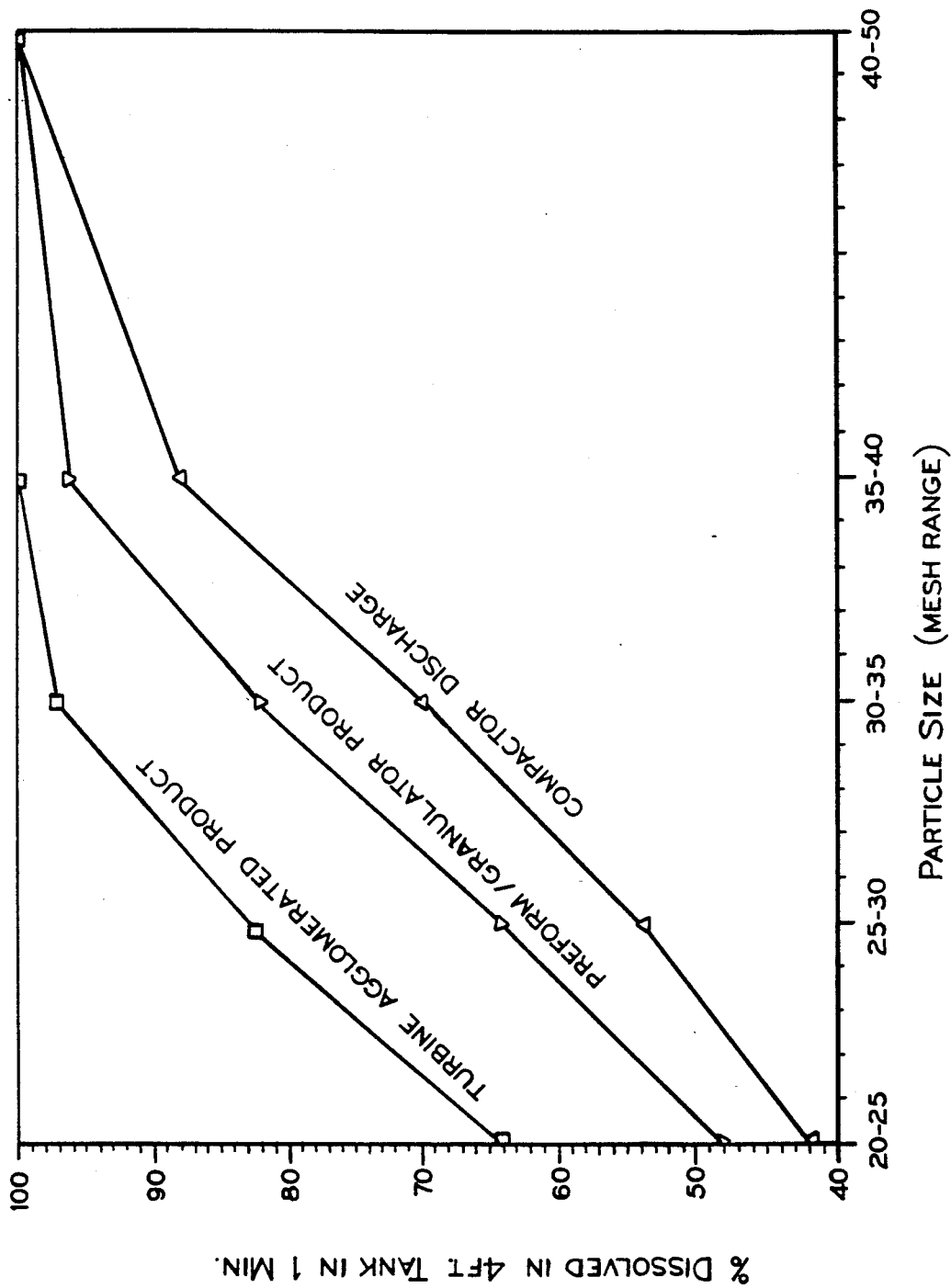
FIG. 4 is a graphic illustration of the dissolving rates of different size particles of calcium hypochlorite produced by different manufacturing processes.

Particles produced in a turbine agglomerator in the instant process dissolve considerably faster than those produced from other conventional processes, as reflected in FIG. 4. This faster dissolvability is the result of several factors.

This graph reflects the fact that agglomerated product particles dissolve significantly faster at each sieve cut or mesh size than product formed from a process employing preforming rolls and a granulator. The graph in FIG. 4 represents the percentage of product particles that dissolve in a tank that is filled with four feet of water and maintained at a water temperature at about 76° F. The predetermined quantity of the calcium hypochlorite particles, such as a 5 gram sample, is poured or scattered on the surface of the water. After one minute, testing is done by sampling to determine from top to bottom the undissolved particles. As shown in FIG. 4, greater than about 82% of the particles of between about 20-35 mesh size having a bulk displacement density determined by volume displacement of about 2.0 grams per milliliter or less dissolved in one minute when scattered on the surface of the water in the four foot deep tank.

The particle bulk density measured by volume displacement in a suitable inert liquid, as described hereafter, correlates with the dissolving rate, regardless of the process used to produce the particles. It was determined during testing that this dissolving rate is a direct function of the particle size, the degree of compaction of the material forming each particle, and the shape of the product particles. To achieve a rapidly dissolving product, it has been determined that the density of 25-30 mesh size particles should be about 2.0 grams per milliliter and preferably less than about 1.95 grams mililiter using saturated aqueous solutions of calcium hypochlorite as the inert liquid in determining the particle displacement bulk density. Turbine agglomerated particles produced, for example, in an 8 inch diameter turbine agglomerator appear to consistently dissolve faster than product produced by other processes, such as preform rolled and granulated, crushed preform rolled and granulated, or dust compacted processes.

Although final particle size and dissolving rates may vary, it appears that adhesion and surface tension of the liquid film formed on the individual hydrated calcium hypochlorite particles may be the key to achieving agglomeration. The adhesion of the liquid film holds the individual particles or crystals together in a moist agglomerate. The thickness of the liquid film or surface moisture layer between the individual particles or crystals before exposing the agglomerated calcium hypochlorite particles to drying is determined by surface tension. It appears that surface moisture, or the thickness of the liquid film between the individual particles forming the agglomerate, rather than the composite moisture of the total agglomerate, is instrumental in forming a fast dissolving product. It is theorized that a relatively thick surface moisture layer is needed to properly agglomerate dust and other small particles on the surface of the agglomerated particle to achieve a fast dissolving particle with a lower density. The dust and other small particles are held together in spaced relationship by the adhesion and surface tension forces, respectively, which are created by the layer of surface liquid present. It is the distance between the spaced apart small particles in the agglomerated particle and the distances between the larger individual particles or crystals that are part of the agglomerates which have a substantial impact on the final particle density and dissolving rate after drying.

The layer of surface liquid should be at least about 16 to about 26% of the particle weight of the agglomerate before drying to minimize density, while still maintaining small particle sizes. Surface liquid layers above 26% of the particle weight can produce agglomerates that are fast dissolving, but there will be oversized agglomerates. This surface liquid layer results from liquid that is either already present in the material to be agglomerated or from liquid that is added to the material through an appropriate liquid inlet in the turbine agglomerator.

A process employing preform pressure rolls squeezes more moisture from between the crystals and thereby causes a much denser particle, which sinks more rapidly and dissolves more slowly in a body of water. Particles formed by rotary drum agglomeration appear to be moderately denser, therefore sinking more rapidly and dissolving more slowly than turbine agglomerated particles. In contrast, a turbine agglomeration process produces faster dissolving particles than either preform pressure roll or rotary drum agglomeration processes.

The thickness of the surface layer of liquid or the liquid film also appears to determine the final porosity of the agglomerate product. This final porosity is also directly correlated to the final dissolving rate of the product. The faster dissolving rate appears to result from the fact that the higher surface moisture found in turbine agglomerated particles spaces the dust and small particles farther apart during agglomeration and subsequent drying. This greater space reduces the amount of compaction or force applied to the particles and leaves the pores essentially intact and large after drying, since the moisture evaporates from within the particle. This results in a less dense and faster dissolving particle. This same mechanism appears also to produce particles with greater surface deformation and, hence, greater exposed external particle surface area.

Figure 16:
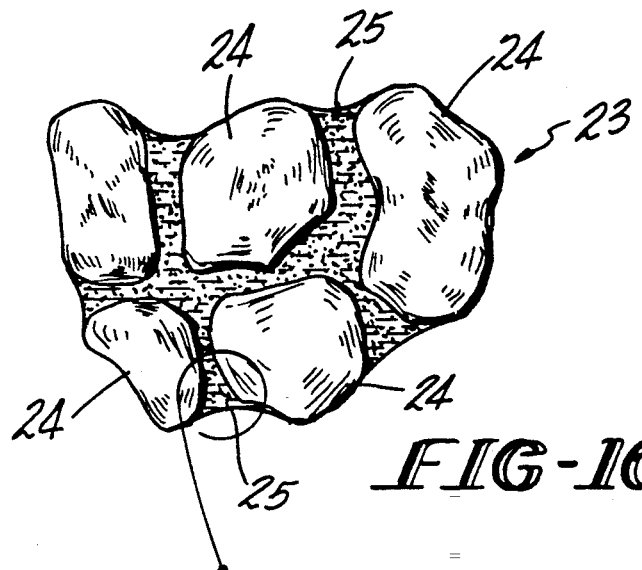
FIG. 16 is a diagrammatical illustration of an agglomerated particle of calcium hypochlorite produced by a turbine agglomerator showing individual particles bound together by the liquid film layer.
Figure 17:
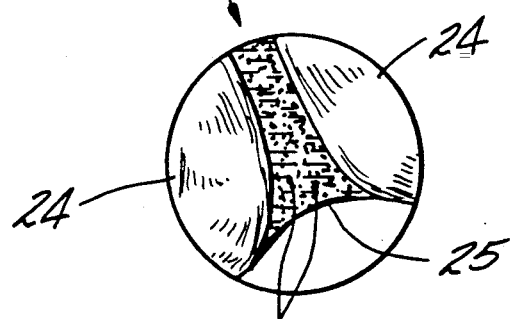
FIG. 17 is an enlarged diagrammatical illustration of the junction of two individual particles in the agglomerated particle of calcium hypochlorite shown in FIG. 16 where the individual particles are bound together by a layer of liquid film.
Figure 18:
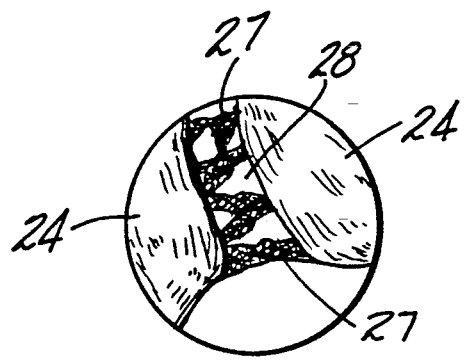
FIG. 18 is an enlarged diagrammatical illustration of the junction shown in FIG. 17 after the particle has been dried and the liquid film layer has recrystallized, showing the connecting bridges or links of calcium hypochlorite joining together the individual particles.

FIGS. 16-18 diagrammatically show the theory behind the functioning of this surface layer of liquid on the agglomerated particle. FIG. 16 shows a turbine agglomerated particle 23 with the individual particles or crystals 24 of calcium hypochlorite held together by liquid film or surface layer 25. FIG. 17 shows in enlarged fashion how this liquid film 25 serves as a binder between portions of two other particles. The adhesion and surface tension forces of this liquid film 25 holds dust and small particles 26 of calcium hypochlorite, as well as the larger individual particles 24, together in a moist agglomerated particle 23.

The thickness of the liquid film 25 determines the distance between the individual particles 24 and the resulting porosity. This, in turn, helps determine the density of the agglomerated particle 23 and, as explained above, its dissolving rate. FIG. 18 diagrammatically illustrates how bridges or connecting links 27 remain between the individual particles 24 of calcium hypochlorite after the moist agglomerated particle 23 is dried, having substantially evaporated the surface layer of liquid film 25 and having had recrystallization occur. The spaces between these connecting links 27 and the individual particles 24 form the pores 28 that promote faster dissolving.

FIG. 5 shows the relationship of particle density after drying measured by bulk displacement versus the percentage of dissolved particles in a tank filled with four feet of water and tested for one particular particle size ranging from 25-30 mesh or about 710 to about 600 microns. In this test the particles' specific gravity or displacement bulk density was maintained less than about 2.0 grams per milliliter and preferably less than about 1.95 grams per milliliter to give the significant dissolving rate improvements achieved. It was found that the particles' density also increases gradually as particle size decreases because the smaller agglomerates approach the size of simple crystals which have a density of about 2.35 grams per milliliter for hydrated calcium hypochlorite.

The thick surface moisture or liquor layer before drying, as previously stated, is the key to forming a fast dissolving particle. Crystallization of the calcium hypochlorite and NaCl within the surface liquor forms the final bridges or connecting links between the individual particles that form the agglomerated product. The length of these bridges help determine the dried agglomerated particle density and dissolving rate.

As presented earlier, adhesion and surface tension forces between the individual particles are the key mechanisms in the agglomeration process before drying the particles. The individual particles are held together in the agglomerated particle by these adhesion forces. Spacing between the small particles in the larger agglomerated particle is determined by the surface tension in the surface moisture layer. When sufficient surface tension is present between the particles being agglomerated, the instant process permits dried dust to be agglomerated onto the particles with a water or appropriate solution mist. Too thin of a layer of surface liquid will result in more dense particles and also the creation of more dust because of lower particle integrity due to less binder, that is the layer of surface liquid, between the small individual particles of calcium hypochlorite. The dust particles hydrate gradually, sometimes sticking to the walls of the turbine agglomerator 10. As the agglomeration process continues, the particles agglomerate into beads large enough to resist sticking to the walls and the particles are easily then agglomerated into the final agglomerate product. These beads of agglomerated particles occur when the total water content is about 28% by weight for both water agglomeration and solution agglomeration, such as filter cake mother liquor, techniques. It is estimated that the surface liquid layer comprises at least about 16% by weight of this total water content.

Good agglomeration of fines or dust and good dissolvability appears to be directly influenced by the water addition rate and the moisture of the feed particles sent into the turbine agglomerator. Moisture control also determines the size of the product particles. More on-size or particles of the proper or desired size range are obtained when moisture control is maintained at the desired level. The revolutions per minute (rpm) of the paddles on the rotatable shaft axially extending through the drum of the turbine agglomerator 10 can affect the final product's dissolvability performance. The production of a greater percentage of on-size product minimizes product handling loads and minimizes fines generation and compaction, as well as reducing the recycle, crushing, and compaction load during product classification.

At 800 rpm paddle rotation in a 30 inch diameter turbine agglomerator, most of the feed, at about 26 to about 28% moisture by weight, into the turbine agglomerator 10 becomes a moist powder within the size range of about 70-100 mesh. A water addition rate of about 0.5 to about 0.8 gallons per minute ensures agglomeration of the powder into particles that are predominantly in the 20 to 50 mesh size range particles. Final product particles of good dissolvability and density were also achieved at 400 and 600 rpm.

The turbine agglomerator 10 functions both as a disintegrator and an agglomerator, even permitting control of agglomeration of particles of very small size. A shearing action exists within the agglomerator 10 from its inlet end to its outlet end which is controlled primarily by the rotational speed and angular orientation of the paddles 11 as they rotate about the shaft 12, best seen in FIG. 7. The agglomerator 10 has a generally circularly shaped drum 14 inside of which paddles 11 rotate. A liquid inlet 15 protrudes through the drum 14 into the interior of the agglomerator 10. Progressive growth of product particles past the maximum size is controlled by the angle of the paddles 11, speed of rotation of the paddles 11, and the clearance between the sidewall of the drum 14 and the individual paddles 11. Agglomerated particles achieve the required shape and sufficient surface strength to remain a particle within a very short period of time, as short as about one second holdup or residence within the turbine agglomerator 10. The turbine agglomerated particles, therefore, are much smaller than standardly produced commercial particles and resist dusting because of sufficient surface strength and integrity.

The angle of paddles 19, 20 and 21 from the inlet end 16 to the outlet end 18 is shown in FIG. 6. The inlet and outlet ports, 13 and 17, respectively are shown with arrows to diagrammatically illustrate the flow of material into and out of the turbine agglomerator 10. Shaft 12 has about eighteen sets of paddles mounted in four rows about the shaft 12. Approximately the first seven paddles 19 are angled forwardly at the angle seen in FIG. 6 to axially convey or transport feed material, representatively of the composition shown in Table I earlier, into the drum 14 of the agglomerator 10. Thereafter a desired number of paddles 20 are positioned or oriented generally axially within the agglomerator 10 to breakup large clumps of calcium hypochlorite and compact the particles.

In a horizontally positioned agglomerator 10, paddles 20 would be angled so that their flat surfaces are generally horizontally positioned with respect to the ground. Similarly, in a vertically positioned agglomerator with the long axis of the drum 14 of the agglomerator positioned generally vertically, the paddles 20 would be angled so they have their flat surface oriented generally vertically with respect to the ground. The greater the number of axially oriented paddles 20, the greater will be the breaking up or crushing, agglomeration and compaction. More axially oriented paddles 20 also increase powder generation and reagglomeration. At higher speeds or revolutions per minute, the greatest effect on the product particles appears to be the reduction of oversized particles and powder generation. Higher speed has a lesser effect on increasing or decreasing the dissolvability of particles.

Rather, the dissolvability of particles appears to be affected directly by the number of axially oriented paddles 20 employed. For example, in a 30 inch diameter turbine agglomerator at 600 rpm, four such paddles 20 in each row of paddles were the maximum employed where good crushing and agglomeration was achieved with minimal compaction. In contrast, at 800 rpm only two axially oriented paddles 20 in each row of paddles were required to achieve both good crushing and agglomeration with minimal compaction.

Downstream of the axially oriented paddles 20 are a second series of forwardly angled paddles 19', only one of which is shown, to convey the particles toward the outlet end 18 of the drum of the agglomerator, as illustrated in FIG. 6. At least a single axially oriented paddle (not shown) may be employed over the outlet 17 of the agglomerator 10, depending upon the size of the outlet, to facilitate directing the particles out of the outlet.

The last paddle 21 can be angled toward the front or inlet end 16 of the agglomerator 10 to prevent the build up of material along the back wall adjacent outlet end 18. The use of the turbine agglomerator 10 in the process to produce hydrated calcium hypochlorite accomplishes substantial shearing action at the inlet end 16 to de-lump or otherwise breakup feed material and then maintains sufficient shear through the agglomerator 10 as the feed material is centrifugally rotated and axially transported to produce only small agglomerates of the desired size, porosity and density.

It has been found that the water addition through the liquid inlet 15 should be accomplished at a point downstream of the axially oriented paddles 20 to minimize the compression or compaction of the product particles that adversely affects the dissolvability of the final product. This positioning of the liquid inlet 15 is best illustrated in FIG. 6. The water addition rate generally depends on the feed particle moisture level, but should be about 0.8 to about 0.6 gallons per minute at about 27% to about 28% water by weight feed particle moisture, respectively for a 30 inch turbine agglomerator 10. At this rate of water addition the feed moisture content of the particles going into the final dryer in the process will be raised by about two percentage points.

Water addition is instrumental in permitting product dust or fines to be circulated into the agglomerator 10 and be successfully agglomerated into on-size particles. Prior processes typically have employed dust that has been generated by the disintegration of particles with insufficient surface liquid for agglomeration. The dust is typically compacted and recrushed. As reflected in FIG. 4, product particles coming from a dust compactor are denser and dissolve more slowly than other hydrated calcium hypochlorite particles in a tank test with four feet of water. The use of the agglomerator 10 with a controlled water addition rate removes the need for fines compaction and, therefore, substantially increases the rapid dissolvability of the product particles.

The use of the turbine agglomerator 10 in existing hydrated calcium hypochlorite production processes can obviate the need to preform the filtered cake feed by the use of high pressure rolls. The removal of the need for the high pressure preform rolls and the granulators that are necessary to break up the filter cake can greatly simplify the process. Maintenance problems are also reduced substantially. Further, and perhaps most significantly, the removal of the need for preform rolls and granulators produces a product that is faster dissolving within the desired particle size range. As reflected in FIGS. 4 and 5, it is clearly seen that the product produced by turbine agglomeration is faster dissolving in a tank that is filled with four feet of water.

FIG. 5 reflects the effect of density determined by displacement bulk density on the dissolving rate of the turbine agglomerated particles one minute after the particles were scattered on the surface of the water in the tank. The desired density is between about 1.0 grams per milliliter to less than about 2.0 grams per milliliter and preferably less than about 1.95 grams per milliliter. The portion of the graph in Area A represents turbine agglomerated particles. The second data point at about 1.91 g/ml represents turbine agglomerated product which was formed from a feed material with an inlet moisture of about 6%, which is too low. The portion of the graph in Area B represents particles formed by rolling bed agglomeration in which feed material which was either dry or premoistened was fed to an unflighted 12 inch rotary drum into which moisture was added. The portion of the graph in Area C represents particles formed by use of preform rolls to compress the feed material and a granulator to break it up into smaller particles in the typical prior commercial processes.

The displacement bulk density of hydrated calcium hypochlorite particles is measured by a standard method, such as ASTM Method C493-70 (Standard Test Method for Bulk Density and Porosity of Granular Refractory Materials by Mercury Displacement), in which a liquid inert to calcium hypochlorite is substituted for mercury and the heating step to remove water of hydration is eliminated. Suitable inert liquids include saturated aqueous solutions of calcium hypochlorite and orthodichlorobenzene.

The measurement of displacement bulk density is generally described as follows:

A graduate is filled to an initial level with the inert liquid and the volume recorded. A sample of hydrated calcium hypochlorite particles is weighed and the weight recorded. The particles are gradually added to the graduate while gently stirring the slurry. After addition of the particle sample, the final volume is recorded. The displacement bulk density is calculated from the following formula:

$$\text{Displacement Bulk Density (g/ml)} = \frac{\text{Weight of Crushed particles (grams)}}{\text{Final Vol. (ml)} - \text{Initial Vol. (ml)}}$$

Particle porosity has a marked effect on the dissolving rate of product particles. This is related to the increased surface area of each particle and the exposure of more of each particle to water. The surface area is increased from two sources; increased surface deformation and internal gaps or pores within each agglomerated particle. These internal gaps or pores within each agglomerated particle are also characterized by the aforementioned bridges or links that develop when the surface liquor is evaporatored during drying. The porosity of the product particles and the sizes of the pores can be measured in a mercury intrusion porosimeter, such as a Model 9200 Autopore manufactured by Micromeritics. Hydrated calcium hypochlorite particles produced by the compressive techniques of preformed or pressure roll processes currently commercially employed, as well as particles produced by rolling bed or spray graining and turbine agglomeration techniques, can be measured by this device.

Mercury intrusion porosimetry functions by first evacuating a particulate sample and then back filling the particle with mercury under pressures up to 60,000 pounds per square inch. This high pressure must be used to squeeze mercury into the pores since the mercury has a negative contact angle and will resist intrusion into such pores in the hydrated calcium hypochlorite particles.

The amount of pressure and accurate measurements of the volume of mercury utilized give the number of pores of each size in the particulate sample. Bulk densities measured by mercury intrusion porosimetry tend to be lower than that measured by the displacement bulk density method because of the relative resistance of the mercury to intrusion. It has generally been observed that the filter cake mother liquor used in the hydrated calcium hypochlorite production processes described herein in a displacement bulk density test fills about 50 to about 95% of the volume of the surface deformities and pores which are not filled by mercury in a mercury intrusion porosimetry test method to determine bulk density.

Table II shows the effect of increased surface deformation and porosity measured by mercury intrusion porosimetry on the dissolving rate of four hydrated calcium hypochlorite samples produced from feed pastes of the same composition as that seen in Table I by a conventional pressure or preform roll/granulation commercial process, a pressure or preform roll/granulation process with the product crushed prior to dissolving, a rolling bed agglomeration process and a process of the instant invention employing turbine agglomeration. Samples between 25-30 mesh sizing were scattered on the surface of a tank filled with four feet of water and the amount dissolved after one minute was recorded. Reflecting the porosity of the particles, the desired surface deformation of turbine agglomerates measured by mercury intrusion porosimetry is greater than about 26% to about 32%. The bulk density of turbine agglomerates measured by the same method is preferably less than about 1.39 grams per milliliter and greater than about 1.0 grams per milliliter.

formation by compressive techniques, such as pressure or preform rolling.

The process shown in FIG. 1 is exemplary of the type of process that can employ a turbine agglomerator in lieu of pressure or preform rollers and granulators. In this process a calcium hypochlorite cake of the alternate composition discussed with reference to Table I for an expression filter is made from paste and fed through a suitable separation device, such as a centrifuge or expression filter to reduce the water content to about 30 to about 40% by weight. The filtered cake is then fed to an appropriate crusher, if needed, which breaks up the cake to a size and texture suitable for feeding into a turbine agglomerator. A turbine agglomerator in many cases can accomplish the needed crushing of the feed material, obviating the need for a crusher depending upon the size, moisture and hardness of the feed material.

Water or an aqueous solution is fed into a turbine agglomerator of, for example, 30 inch diameter at a desired rate, normally from about 0.0 gallons per minute where no liquid is added because of the excessive moisture of the feed material to about 0.8 gallons per minute for a feed material comprised of both dust and crushed cake, the mixture discharged from the agglomerator having about a 28 to 31% by weight water content and a feed rate of the dust and crushed cake of about 8500 pounds wet basis per hour. The feed of the crushed cake per unit of time up to the capacity of the turbine agglomerator is primarily limited by the drying capacity of the final dryer. The agglomerated particles are then fed to a mechanically gentle dryer, such as a tray dryer, for final drying to a water content of less than about 10% by weight, but preferably from about 8.5% to about 5.5% by weight. The dryer temperature is maintained from about 280° F. to about 320° F. and can be as high as about 350° F., employing a residence time of about 2 hours. Screens are employed to size the product particles to the desired size, normally 20-50 mesh. Oversized and undersized product particles are fed back into the process immediately upstream of the size reducer or crusher. Dust and fines from other areas in the production process are also recycled into the process at this point.

The process outlined according to FIG. 1 produces a

TABLE II

| Sample | Mercury Porosimetry Particle Data | | | Displacement | |
| | Average pore diameter (microns) | Surface Deformation (% of Total pore volume) | Bulk Density (g/ml) | Bulk Density (g/ml) | % Dissolved |
| --- | --- | --- | --- | --- | --- |
| Preform roll/ granulated | 0.0342 | 13 | 1.77 | — | 61 |
| Preform roll/ granulated/crushed | 0.0385 | 13 | 1.71 | 2.33 | 60 |
| Rolling bed agglomeration | 0.0578 | 26 | 1.39 | 2.09 | 71 |
| Turbine Agglomeration | 0.1319 | 32 | 1.30 | 1.88 | 87 |

Agglomerated particles produced by the novel process of the present invention rapidly dissolve in water bodies, such as swimming pools, while leaving a minimal amount of undissolved residue materials on the pool bottom or walls. The agglomerated particles dissolve significantly faster than irregularly shaped non-agglomerated calcium hypochlorite particles produced by known commercial processes employing particle faster dissolving product from a cake of hydrated calcium hypochlorite that has been treated by high expression filters than do prior commercial processes, whether employing high expression filters or not.

Figure 2:
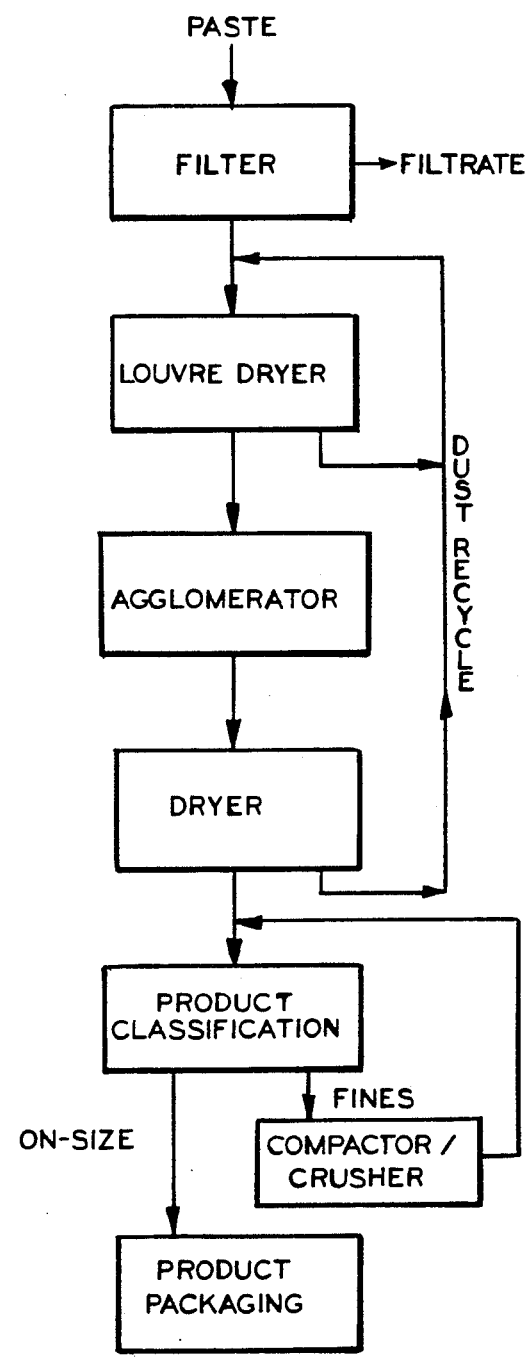
FIG. 2 is a diagrammatic illustration of an alternate process that may be used to make hydrated calcium hypochlorite.

FIG. 2 shows a alternate process where a normal filter can be used to receive a hydrated calcium hypochlorite paste of the type used to form the cake of the composition discussed with reference to Table I. The paste is sent through a suitable separation device, such as a filter to produce a cake with about a 43 to a 47% moisture content. The filtered cake may be blended with recycled dust and then is sent to a louvered dryer with a temperature of about 280° F. to about 320° F. or as high as about 350° F. at the inlet and a residence time of about 50 minutes. The dried discharge, with about 25% to about 30% water, is fed directly into the inlet 13 in a turbine agglomerator 10 where water via the inlet 15 is added at a predetermined rate immediately before the second set of angled paddles 19' and after the last of the generally axially oriented paddles 20 of FIG. 6. This predried product encounters the rotating paddles of the turbine agglomerator which is operated at about 800 rpm per minute in a 30 inch diameter drum. If an eight inch turbine agglomerator is utilized, the paddles are rotated at 1800 rpm. The agglomerated product is then sent to a mechanically gentle dryer, such as a tray dryer, where it is dried for two hours with an inlet temperature of about 280° F. to about 320° F. or as high as 350° F. The product exits the dryer with a moisture content of less than about 10% by weight and preferably of about 6.5% moisture by weight. The dried product is then classified according to size and off-size product is recycled through a crusher and then reclassified. Fines are sent through a compactor and crusher and then recycled through product classification.

Figure 3:
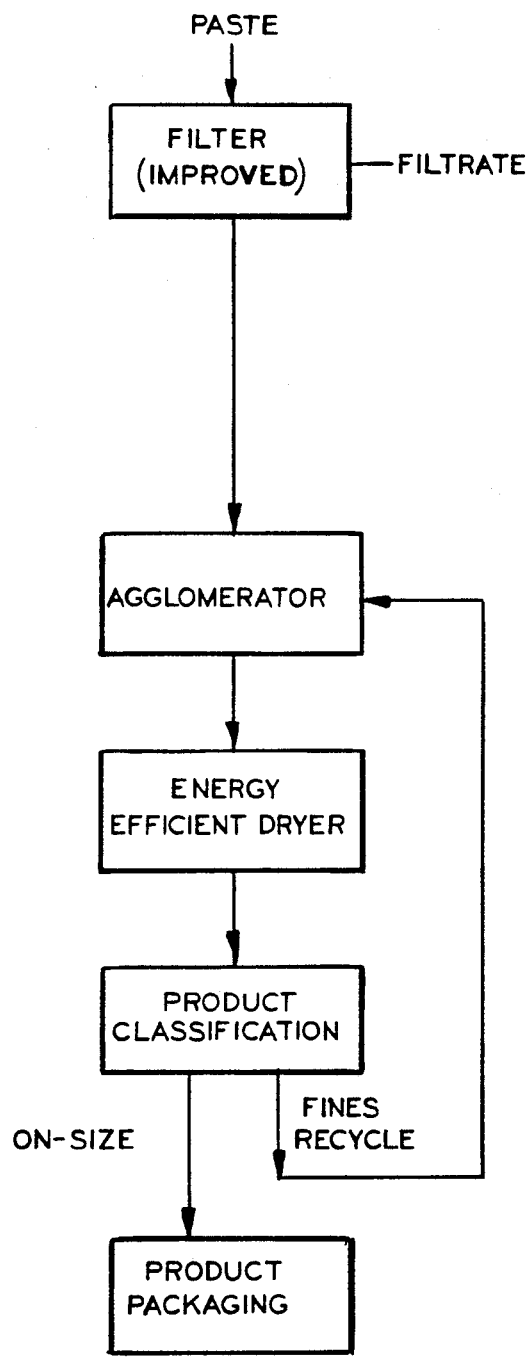
FIG. 3 is a diagrammatic illustration of a second alternate process that may be employed to produce hydrated calcium hypochlorite.

A second alternate process employing high pressure expression filters is shown in FIG. 3 wherein a calcium hypochlorite paste used to form a cake of the alternate composition discussed with reference to Table I is fed into the expression filter to reduce the moisture of the paste down to the level described in the process of FIG. 1. The paste or cake is fed directly to turbine agglomerator 10 with or without mixing of dry dust material. The turbine agglomerated product exits the agglomerator with a moisture of about 28 to about 31% by weight and is fed to an energy efficient dryer, such as a fluid bed dryer with a uniform temperature ranging from about 235° F. to about 265° F. and a residence time of about 30 minutes. This type of a fluid bed dryer is characterized by a good heat transfer coefficient between the product particles and the air because of the higher velocity of the air with respect to the particles. The final dried particles have a water content of less than about 10% by weight and preferably from about 8.5% to about 5.5% by weight. The dried particles are then fed to a product classifier, such as screens, where on-size product is removed and off-size product is recycled back through a crusher and reclassified or returned to the agglomerator. Fines are recycled back into the turbine agglomerator.

The following examples are presented to illustrate the novel process of the present invention without any intention of being limited thereby. All parts and percentages are by weight unless otherwise specified.

EXAMPLE 1

Dry calcium hypochlorite fines with about a 6% water content and about a 70% available chlorine content in the size range of 50 to 150 mesh were fed at a rate of 926 pounds per hour to a pilot scale eight inch diameter turbine agglomerator. The balance of the material was predominately NaCl with trace amounts of other calcium salts, such as $CaCl_2$, $Ca(ClO_3)_2$, $Ca(OH)_2$ and $CaCO_3$. Water was simultaneously injected into the turbine agglomerator at a rate of 15 gallons per hour near the infeed end. This resulted in a final product moisture of about 19.3% water. Well formed agglomerates were produced and then dried in a laboratory vacuum oven for about 2½ hours to a dried or product moisture of 4% water.

Prior to drying in the laboratory vacuum oven the product particle temperatures were recorded as ranging from about 75° F. to about 160° F. This high temperature was attributed to the hydration of the calcium hypochlorite crystals.

The dried product particles were sieved to a predetermined size. The sizing range had a particle distribution of about 27.9% greater than 20 mesh, about 62.8% ranging from between about 20 to about 50, mesh and about 9.3% size less than 50 mesh. The product was further sieved to discrete size ranges of 20-25 mesh, 25-30 mesh, 30-35 mesh, and 35-40 mesh. A sample of each size range was scattered on the surface of a tank filled with four feet of water and found to dissolve in one minute significantly faster than particles produced by a conventional commercial process utilizing preform pressure rolls and granulation. The displacement bulk density of the 25-30 mesh cut product was measured to be about 1.91 grams per milliliter.

EXAMPLE 2

Wet calcium hypochlorite cake with about 32% moisture and about 61% available chlorine was fed at a rate of 1000 pounds per hour to an eight inch diameter turbine agglomerator. The balance of the feed material was predominately NaCl with trace amounts of other calcium salts, such as $CaCl_2$, $Ca(ClO_3)_2$, $Ca(OH)_2$, and $CaCO_3$. Simultaneously, dry calcium hypochlorite fines with about 6% water content were fed at a rate of 182 pounds per hour. Negligible heat of hydration of the dust particles was observed because of the larger mass of the wet cake feed. Very well formed agglomerates of about 28% water content were produced and then were dried in a four square foot fluid bed dryer operated at about 250° F. The particles were dried for about 30 minutes to reach about 8.1% water content.

The dried product was sieved and found to have a particle distribution of about 15.6 percent in size greater than 20 mesh, about 72.4% between the size 20 and 50 mesh, and about 12.0 % less than size 50 mesh.

The product was further sieved to discrete size ranges of 20-25 mesh, 25-30 mesh, 30-35 mesh, and 35-40 mesh. A sample of each size range was scattered on the surface of a tank filled with four feet of water and found to dissolve in one minute significantly faster than particles of the conventional commercial processes. The displacement bulk density of the 25 to 30 mesh cut was measured to be about 1.88 grams per mililiter. These particles had an average pore diameter of about 0.132 microns and a mercury porosimetry bulk density of about 1.30 grams per milliliter. About 32% of the total pore volume was on the surface of the agglomerated particles.

EXAMPLE 3

Predried calcium hypochlorite material with about a 26 to about a 28% water content and between about 54% to about 59% available chlorine was fed to a turbine agglomerator with a 30 inch diameter. The balance of the feed material was predominately NaCl with trace amounts of other calcium salts, such as $CaCl_2$, $Ca(ClO_3)_2$, $Ca(OH)_2$ and $CaCO_3$. The agglomerator was operated with the blades turning at about 800 rpm. The feed rate of particles into the turbine agglomerator was about 8500 pounds per hour dry basis simultaneously with a water infeed of about 0.6 to about 0.8 gallons per minute fed into the agglomerator immediately after the axially oriented paddles 20 and before the second set of forwardly oriented paddles 19' seen in FIG. 6. Very well formed agglomerated product particles were produced with a discharge moisture of about 30–31% water. The particles were continuously discharged into a commercial scale convection dryer. Particles were dried to about 5–8% moisture in about 90 to about 120 minutes. The dried product particles were sieved and found to range from about 40% greater than 20 mesh, about 40% between 20 and 50 mesh, and about 20% less than 50 mesh. A composite of the sieved product between 20–50 mesh dissolved about 85–90% in one minute in four feet of water.

The product particles were then further sieved to discrete size ranges of 20–25 mesh, 25–30 mesh, 30–35 mesh, and 35–40 mesh. A sample of each size range was scattered on the surface of a tank with four feet of water and was found to dissolve in one minute significantly faster than particles produced by current commercial processes. This relative dissolving rate is shown in FIG. 4. The displacement bulk density of the 25–30 mesh cut particles was measured to be about 1.89 grams per milliliter.

COMPARATIVE EXAMPLE A

A calcium hypochlorite filter cake of the composition shown in Table I earlier was processed in a conventional, commercial process which included preforming by high pressure roll compaction, granulating into flakes and drying on tray dryers. The irregularly shaped, non-agglomerated flakes had an available chlorine content of about 74%, a moisture content of about 7.3% water, and a displacement bulk density of about 2.33 grams per milliliter. These particles had an average pore size of about 0.034 microns and a mercury porosimeter bulk density of about 1.77 grams per milliliter. Only about 13 percent of the pore volume of these particles was located on the surface. The product flakes were screened to 20 to 50 mesh. When scattered on the surface of a tank filled with four feet of water using the procedure employed in Examples 1-3, only about 75% of the flakes dissolved in one minute, whereas the turbine agglomerated product dissolved significantly faster at all mesh sizes, as seen in the graphical illustration in FIG. 4.

COMPARATIVE EXAMPLE B

Commercially produced hydrated calcium hypochlorite granules used in Comparative Example A were screened to provide three different granule size ranges of about 1000 microns (18 mesh), about 710 microns (25 mesh) and about 500 microns (35 mesh). A sample of each of these sizes of commercially produced Ca(OCl)$_2$ particles were scattered on the surface of a tank filled with four feet of water using the procedure of Examples 1-3. After one minute, the percent of dissolved particles at about 1000 microns was determined to be only about 34% of the granules. At about 710 microns only about 54% of the granules were dissolved after one minute. At about 500 microns only about 77% of the granules were dissolved after one minute. Turbine agglomerated product particles at comparable sizes dissolved significantly faster, as illustrated by the turbine agglomerated product plot in FIG. 4.

Figure 8:
FIG. 8 is a scanning electron photomicrograph with a magnification factor of 72 of hydrated calcium hypochlorite agglomerated particles produced by a representative process employing a turbine agglomerator.
Figure 9:
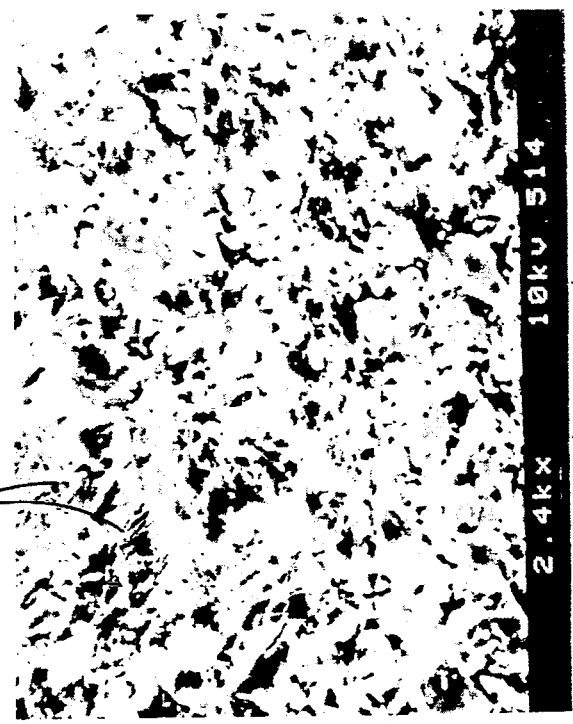
FIG. 9 is a scanning electron photomicrograph with a magnification factor of 2400 of hydrated calcium hypochlorite agglomerated particles produced by a representative process employing a turbine agglomerator.
Figure 10:
FIG. 10 is a scanning electron photomicrograph with a magnification factor of 72 of hydrated calcium hypochlorite particles produced by a typical commercial process employing preform compression rollers, a granulator and a tray dryer.
Figure 11:
FIG. 11 is a scanning electron photomicrograph with a magnification factor of 2400 of hydrated calcium hypochlorite particles produced by a typical commercial process employing preform compression rollers, a granulator and a tray dryer.
Figure 12:
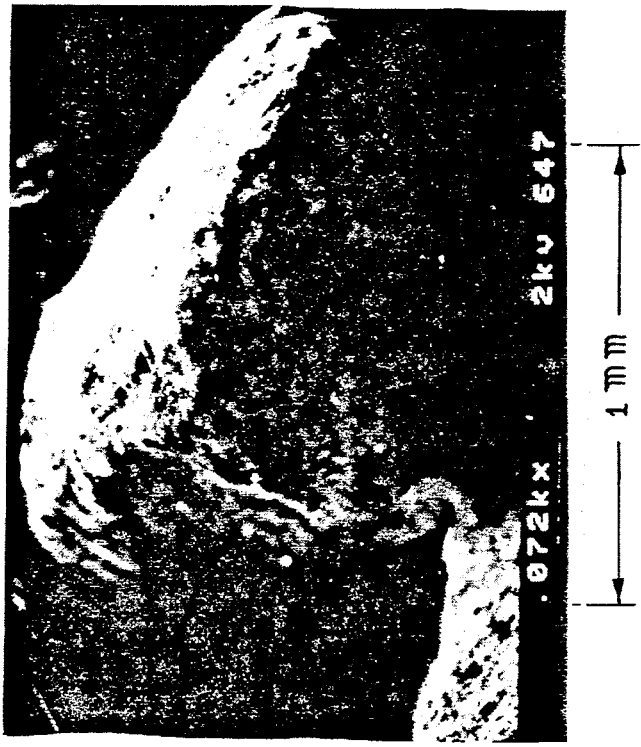
FIG. 12 is a scanning electron photomicrograph with a magnification factor of 72 of compacted dust or fines of hydrated calcium hypochlorite particles produced by a typical commercial process employing preform compression rollers, a granulator and a tray dryer, where the dust or fines have been compacted, crushed and screened according to size.
Figure 13:
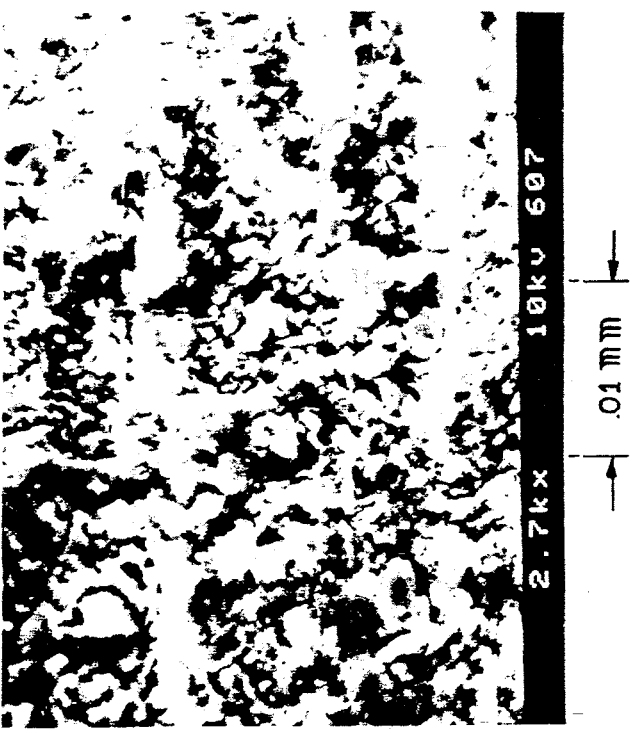
FIG. 13 is a scanning electron photomicrograph with a magnification factor of 2700 of compacted dust or fines of hydrated calcium hypochlorite particles produced by a typical commercial process employing preform compression rollers, a granulator and a tray dryer, where the dust or fines have been compacted, crushed and screened according to size.
Figure 14:
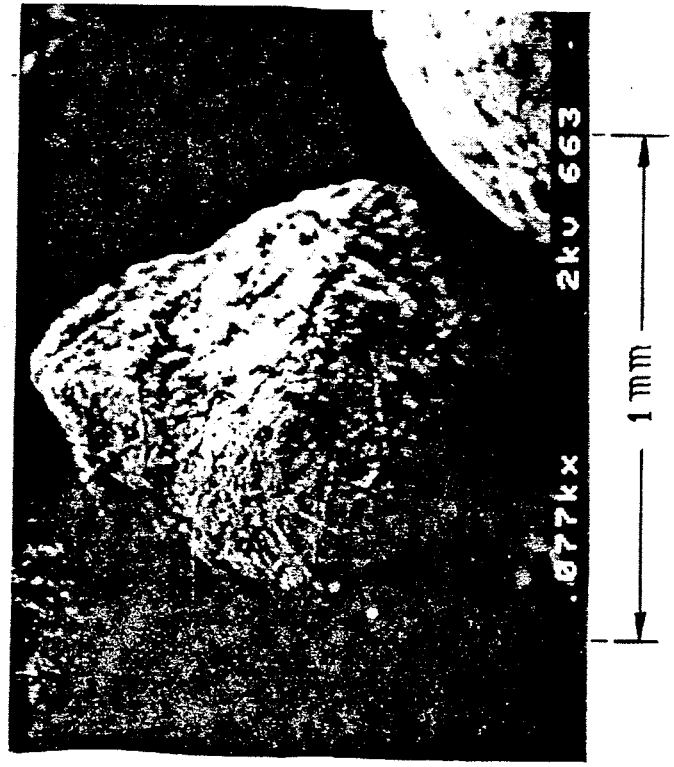
FIG. 14 is a scanning electron photomicrograph with a magnification factor of 77 of hydrated calcium hypochlorite particles produced by a spray graining process in a rolling bed agglomerator.
Figure 15:
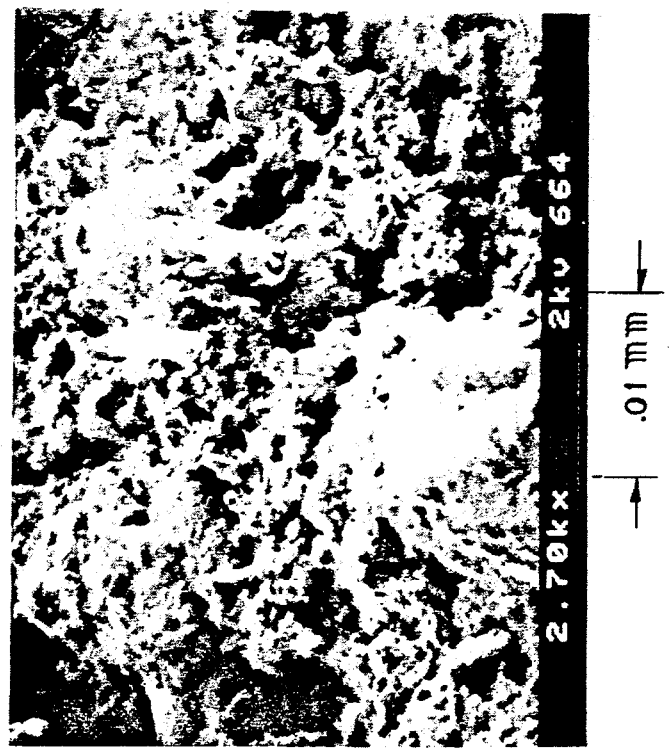
FIG. 15 is a scanning electron photomicrograph with a magnification factor of 2700 of hydrated calcium hypochlorite particles produced by a spray graining process in a rolling bed agglomerator.

FIGS. 8-15 show scanning electron photomicrographs of hydrated calcium hypochlorite particles produced by four different processes, the photomicrographs being sequentially paired by the type of process. Specifically, FIGS. 8 and 9 are turbine agglomerated particles, FIGS. 10 and 11 are preform roll/granulated particles, FIGS. 12 and 13 are particles produced from compacted dust or fines, and FIGS. 14 and 15 are spray grained particles produced in a rotary drum agglomerator. Each type of particle was electron photomicrographed at two separate magnification levels.

FIG. 8 shows at a magnification level of 72 turbine agglomerated particles which have been dried to a final product form. The agglomeration effect of small individual particles being held together to build a larger agglomerate is clearly shown. The relative smoothness of the individual particles of the surface comprising the agglomerates is also clearly shown.

FIG. 9 shows a portion of one of the agglomerated particles of FIG. 8 at a magnification level of 2400. The bridges or connecting links contributing to the highly porous structure of the turbine agglomerated product are clearly visible in the upper left hand corner.

The product shown in FIGS. 8 and 9 was produced from a feed material which had about 29.2% moisture as it entered the turbine agglomerator, experienced about a 0.6 gallons per minute water feed rate in the turbine agglomerator, and was discharged with a moisture level of about 31%. The agglomerated particles were then fed to a tray dryer with an inlet air temperature of about 310° F. The particles exited the tray dryer with a discharge moisture of about 7.88% after a residence of about 90 minutes. The electron photomicrographed particles in FIGS. 8 and 9 were screened to a 25–30 mesh size.

A solubility test in a four foot deep tank with particles ranging in size from 25–30 mesh resulted in 78% of the particles scattered on the surface of the water dissolving within one minute. A five gram sample was scattered on the water, which was maintained at about 76° F.

FIGS. 10 and 11 show scanned electron photomicrographs of hydrated calcium hypochlorite particles produced by a standard commercial process employing preform compression rollers, a granulator and a tray type of final dryer. FIG. 10 shows dried product particles at a magnification level of about 72. FIG. 11 shows a portion of one of the particles of FIG. 10 at a magnification level of about 2400. Protruding platelets of what are probably calcium hypochlorite crystals are clearly visible in FIG. 11. The platelets appear to form a relatively rough surface that is susceptible to fracture and subsequent dusting.

The product shown in FIGS. 10 and 11 was produced from a feed material with about 29.2% moisture and was discharged from the tray dryer with a discharge moisture of about 8.8% in irregularly shaped, non-agglomerated flakes. The electron photomicrographed particles were screened to a 20–25 mesh size.

A solubility test in a four foot deep tank with particles of the type shown in FIGS. 10 and 11 ranging in size from 25–30 mesh resulted in about 63.8% of the particles scattered on the water dissolving within one minute. A five gram sample was scattered on the water, which was maintained at about 76° F.

FIGS. 12 and 13 show scanned electron photomicrographs of compacted hydrated calcium hypochlorite particles produced from the fines or dust generated by a standard commercial process which employs preform compression rollers and granulators. The dust is recycled to a compactor and then recrushed, thereby forming product particles which were classified according to size.

The compacted product particles shown in FIGS. 12 and 13 come from dust or fines with a moisture content of about 6% to about 7%. The electron photomicrographed particles were screened to a 20-25 mesh size.

FIG. 12 shows a representative sample of compacted commercial product particles at a magnification level of about 72. FIG. 13 shows a representative sample of compacted commercial product particles at a magnification level of about 2700. Both figures show how the compacted product's surface consists of small, tightly packed grains with little evidence of porosity.

FIGS. 14 and 15 show a representative sample of particles produced by spray graining particles in a rolling bed agglomerator. FIG. 14 shows spray grained particles at a magnification level of about 77 and FIG. 15 shows a portion of the same type of particle at a magnification level of about 2700. The scanned electron photomicrographs in FIGS. 14 and 15 were screened to a 20-30 mesh size.

The product in FIGS. 14 and 15 were produced in a rotary drum agglomerator with a starting or seed bed of calcium hypochlorite particles. A slurry was sprayed into the rotating drum comprised of from about 45% to about 90% by weight of water, preferably from about 50% to about 60% by weight of water. The slurry was obtained from a calcium hypochlorite filter cake produced by a conventional commercial calcium hypochlorite process. The filter cake typically has the analysis and preferred analysis range of the components shown in Table I earlier, expressed as percent by weight.

Forced drying air was inletted into the rotary drum at temperatures ranging from about 260° F. to about 310° F. Bed temperatures of the spray grained particles ranged from about 125° F. to about 140° F.

The particles shown in FIGS. 14 and 15 appear generally rounded and regular in shape, but with a different porous appearance than the particles produced by turbine agglomeration.

While the preferred process and product particle in which the principles of the present invention have been incorporated is shown and described above, it is to be understood that the invention is not to be limited to the particular details thus presented, but, in fact, widely different means and methods may be employed in the practice of the broader aspects of this invention. The scope of the appended claims is intended to encompass all obvious changes in the details, materials, arrangement of apparatus and the process disclosed which will occur to one of skill in the art upon a reading of this disclosure.

Having thus described the invention, what is claimed is:

1. A hydrated calcium hypochlorite agglomerated particle produced in a turbine agglomerator by centrifugally rotating and axially transporting feed material while subjecting the feed material to a shearing action, the agglomerated particle prior to drying being formed from small particles held together at least partially by the surface tension and adhesion forces of a layer of surface liquid comprising at least about 16% to about 26% by weight of the particle prior to drying, at least a portion of the source liquid being provided by moisture in the feed material and the remaining surface liquid being introduced into the turbine agglomerator while the particles are centrifugally rotated and axially transported, the agglomerated particle then being dried to substantially evaporate the layer of surface liquid and to promote recrystallization of the feed material and calcium hypochlorite; the agglomerated particle comprising in combination:
  a) a plurality of connecting links of recrystallized material bridging the small particles and connected thereto; and
  b) a plurality of pores formed by the evaporation of the layer of surface liquid between the small particles to form a highly porous, fast dissolving agglomerated particle, the particle having a size of between about 20 to about 35 mesh and a bulk density determined by volume displacement of between about 1.0 grams per milliliter and about 2.0 grams per milliliter.

2. The invention according to claim 1 wherein the agglomerated particle has a bulk density measured by mercury porosimetry of greater than about 1.0 grams per milliliter and less than about 1.39 grams per milliliter.

3. The invention according to claim 1 wherein the agglomerated particles has a bulk density determined by volume displacement of between about 1.0 grams per milliliter and less than about 1.95 grams per milliliter.

4. The invention according to claim 1 wherein the agglomerated particles has a surface deformation of greater than about 26% and less than about 32% as measured by mercury porosimetry.

5. The invention according to claim 1 wherein the agglomerated particles has a moisture content after drying of less than about 10% by weight.

6. The invention according to claim 5 wherein the agglomerated particles has a moisture content after drying of between about 8.5% to about 5.5% by weight.

7. In a process for the production of hydrated calcium hypochlorite from a feed material consisting of calcium hypochlorite, water, sodium chloride and calcium salts selected from the group consisting of calcium chloride, calcium chlorate, calcium carbonate and calcium hydroxide comprising the steps of:
  (a) feeding the feed material into a turbine agglomerator in which the feed material is centrifugally rotated and axially transported while being subjected to a shearing action which breaks up the feed material;
  (b) agglomerating the particles of the centrifugally rotated and axially transported feed material within the turbine agglomerator into product particles by controlling the layer of surface liquid to at least about 16% to about 26% by weight of the particles prior to drying by adding moisture at a controlled rate and adding dust particles to the feed material in the turbine agglomerator; and
  (c) drying the product particles to evaporate the layer of surface liquid to form a fast dissolving, porous product particle which is formed by connecting links between the agglomerated particles of feed material, the product particle having a particle size of between about 20 to about 35 mesh and a bulk density determined by volume displacement of between about 1.0 grams per milliliter and about 2.0 grams per milliliter.

8. The method according to claim 7 wherein the bulk density determined by volume displacement of the dried porous product is between about 1.0 grams per milliliter and less than about 1.95 grams per milliliter.

9. The method according to claim 7 wherein the agglomerated product particle prior to drying has a moisture content of about 19% to about 32% by weight.

10. The method according to claim 9 wherein the agglomerated particle prior to drying has a moisture content of about 25% to about 31% by weight.

11. The method according to claim 10 wherein the agglomerated particle prior to drying has a moisture content of about 28% to about 31%.

12. The method according to claim 9 wherein the moisture content of the dried porous product is less than about 10% by weight.

13. The method according to claim 12 wherein the moisture content of the dried porous product is from about 8.5% to about 5.5% by weight.

14. The method according to claim 7 wherein the dried porous product has a surface deformation of greater than about 26% to about 32% as measured by mercury porosimetry.

15. The method according to claim 7 wherein the dried porous product has a bulk density measured by mercury porosimetry of less than about 1.39 grams per milliliter and greater than about 1.0 grams per milliliter.

16. The method according to claim 7 wherein liquid is added to the turbine agglomerator during the agglomerating of the particles.

17. A hydrated calcium hypochlorite agglomerated particle produced in a turbine agglomerator by centrifugally rotating and axially transporting feed material while subjecting the feed material to a shearing action, the agglomerated particle prior to drying being formed from small particles held together at least partially by the surface tension and adhesion forces of a layer of surface liquid comprising at least about 16% to about 26% by weight of the particle prior to drying, the agglomerated particle then being dried to substantially evaporate the layer of surface liquid and to promote recrystallization of the feed material and calcium hypochlorite; the agglomerated particle comprising in combination:
a) a plurality of connecting links of recrystallized material bridging the small particles and connected thereto;
b) a plurality of pores formed by the evaporation of the layer of surface liquid between the small particles to form a highly porous, fast dissolving agglomerated particle; and
c) the particle being between about 20–35 mesh size, having a bulk density determined by volume displacement of about 2.0 grams per milliliter or less and dissolving in about four feed of water maintained at about 76° F. in one minute or less greater than about 82% of the time when placed on the surface of the water.

18. The invention according to claim 17 wherein the agglomerated particles has a bulk density determined by volume displacement of between about 1.0 grams per milliliter and less than about 1.95 grams per milliliter.

19. The invention according to claim 18 wherein the agglomerated particle has a moisture content after drying of less than about 10% by weight.

20. The invention according to claim 19 wherein the agglomerated particle has a moisture content after drying of between about 8.5% to about 5.5% by weight.

21. The invention according to claim 17 wherein the agglomerated particle has a bulk density measured by mercury porosimetry of greater than about 1.0 grams per milliliter and less than about 1.39 grams per milliliter.

22. The invention according to claim 21 wherein the agglomerated particle has a surface deformation of greater than bout 26% and less than about 32as measured by mercury porosimetry.

* * * * *

UNITED STATES PATENT AND TRADEMARK OFFICE
CERTIFICATE OF CORRECTION

PATENT NO. : 5,171,562

DATED : December 15, 1992

INVENTOR(S) : William G. Bridges

It is certified that error appears in the above-identified patent and that said Letters Patent is hereby corrected as shown below:

In column 22, at line 14 please delete "feed" and insert --feet-- in its place;

In column 22, at line 35 please delete "bout" and insert --about-- in its place; and at line 35 after the word "about" delete "32as" and insert --32% as-- in its place.

Signed and Sealed this

Twenty-first Day of June, 1994

Attest:

BRUCE LEHMAN

Attesting Officer

Commissioner of Patents and Trademarks